United States Patent [19]

Hämmerling et al.

[11] Patent Number: 4,804,627
[45] Date of Patent: Feb. 14, 1989

[54] METHOD FOR CLONING LYMPHOBLASTOID CELLS

[75] Inventors: Ulrich Hämmerling; Slawomir Kosinski, both of New York, N.Y.

[73] Assignee: Sloan-Kettering Institute for Cancer Research, New York, N.Y.

[21] Appl. No.: 732,370

[22] Filed: May 9, 1985

[51] Int. Cl.[4] .......................... C12M 3/00; C12N 5/00
[52] U.S. Cl. .............................. 435/240.21; 435/240.2; 435/240.25
[58] Field of Search .................. 435/68, 240, 241, 948, 435/244; 935/108

[56] References Cited

U.S. PATENT DOCUMENTS

| | | | |
|---|---|---|---|
| 4,066,510 | 1/1978 | Thilly | 435/241 |
| 4,434,230 | 2/1984 | Ritts, Jr. | 435/241 |
| 4,465,776 | 8/1984 | Cidlowski et al. | 435/68 |
| 4,524,025 | 6/1985 | Geltosky | 435/68 |
| 4,572,896 | 2/1986 | Hampar et al. | 435/68 |

OTHER PUBLICATIONS

Kennett et al., Curr. Topics in Micb. and Immunol. 81, pp. 77–91 (1978).
Watson et al., Journal of Immunology 130(5), pp. 2442–2447 (1983).
Laboisse et al., Cancer Research 41, pp. 310–315 (1981).
Epstein et al., Cancer Research 39, pp. 1748–1750 (1979).
ATCC Catalogue 4th Ed., 1983, Cell Lines, p. 64.

*Primary Examiner*—John Edward Tarcza
*Attorney, Agent, or Firm*—John P. White

[57] ABSTRACT

A method of growing cells, particularly cells transformed by Epstein Barr Virus, in agarose is disclosed. At least one of the agarose layers has human fibroblast cells suspended therein and another layer has irradiated fibroblasts and the particular growing cells suspended therein.

9 Claims, No Drawings

METHOD FOR CLONING LYMPHOBLASTOID CELLS

FIELD OF THE INVENTION

This invention relates to methods of growing cells and increasing their cloning efficiency, especially cells which have been transformed by Epstein Barr Virus (EBV).

PRIOR ART

Sugden and Mark, J. Virol. 23: 503–508 (1977) disclose a single layer method for growoing lymphoblastoid cell lines. While this reference teaches the use of fibroblasts on the bottom of a growth layer, there is no teaching of co-culture in the layer.

BACKGROUND

Kohler and Milstein have provided a method for successful production of monoclonal antibodies, as reported in Nature, 256: 495–497 (1975). This method involves immunization of mice, followed by removal of the mice spleen cells, and fusion of the spleen cells with mouse myeloma cell lines, in a medium containing polyethylene glycol. Screening methods are then used to determine which, if any, of the resulting fused cells, or "hybridomas," produce monoclonal antibodies to a particular antigen.

This technique has not proven to be generally effective in producing hybridomas which, in turn, produce human monoclonal antibodies. As a result, several different approaches have been taken to improve production of hybridomas or other cell lines which produce human monoclonal antibodies.

One line of inquiry involved the fusion of immunized human B lymphocytes with mouse myeloma cell lines, an "interspecies" hybridization. A second line of inquiry involved "intraspecies" fusion, of immunized human B lymphocytes, with either human myeloma, or human lymphoblastoid cell lines. "Interspecies" hybridization allows the use of well-known mouse myeloma lines NS1 or SP2/oAG14. These cell lines offer the advantage of efficient fusion frequency, and high levels of immunoglobulin production, but present the serious problem of preferential loss of human chromosomes. The loss of human chromosomes results in instability of antibody production. Intraspecies hybridization has not been effective either. Fusion frequencies are low, often below $10^{-5}$, and antibody titer is also very low.

Another line of inquiry has been cell transformation by Epstein Barr Virus (EBV). In the EBV transformation method, human cells, especially B lymphocytes are immortalized by in vitro EBV infection. This method has been used to produce human antibodies to synthetic haptens, tetanus toxoid, diptheria toxoid, Rh antigens, influenza virus, human immunoglobulin complexes, *Plasmodium falciparum* antigens, acetylcholine receptor, pneumococci, and cytomegalovirus.

EPV transformation allows development of cell lines which produce a multitude of desired antibodies. Additionally, this method opens the possiblity of expanding the number and range of immune B lymphocytes useful in hybridization. EBV transformed cell lines, when hybridized to human or to mouse myeloma cell lines, give generally higher levels of antibody production than the original lymphobliastoid line.

EBV techniques are of limited use, however. At best, EBV tarnsformed cells have produced low titers of antibody, generally between 1 and 100 ng/ml. Additionally, uncloned lymphoblastoid cells have contributed to instability of antibody production.

The reason why the antibody secretion of lymphoblastoid cells is unstable over time must be seen in the heterogeneity of the fledging cell lines, which results in overgrowth of the culture by unwanted cells. Thus, EBV transformed cell lines nearly always contain cell mixtures with individual growth kinetics. Any change in the heterogeneous mixture, such as a slight acceleration of the growth cycle of the unwanted cell type, leads to domination of the culture by that type of cell, at the expense of the desired clone.

Early cloning can be expected to alleviate this problem. The two methods traditionally used in cloning, i.e., limiting dilution in liquid culture, and colonial growth in semisolid media, however, do not apply to EBV transformed cell with the same efficiency as with, e.g., mouse hybridoma cells. Limited dilution cloning relies on diluting cells to the point where, statistically, there is only one seed cell per culture well, and each culture (or clone) growing from the cell can be regarded as pure for that cell. In laboratory work, it has been found that very few lymphoblastoid cell lines which produce specific antibodies can be adapted to this method.

Lymphoblastoid cells have been grown in liquid culture in direct contact with irradiated fibroblasts, plated on the bottom of culture plates but, heretofore when agarose cultures were used the fibroblasts were separated from the lymophoblastoids, or any other cells to be cloned, by an agarose layer. It is thought that fibroblasts create an environment which supports growth of cells by providing an extracellular matrix, or biomatrix, composed of several types of collagens and other proteins.

Growth in semisolid agarose medium relies upon dilution of cells to the point at which the colonies which grow from single cells suspended in agarose grow separately from each other, such that the colonies are physically distinct. When colonies are size distinguishable under stereo microscopes, they are picked by micropipette and transferred into liquid medium for further growth. The level of cloning efficiency, however, has never exceeded more than about 3% of input cells.

It has now been found that an improvement in the semi-solid agarose method of growing cell clones establishes conditions where much higher frequencies of cell cloning and growth may be obtained. The method comprises using two layers of agarose, where the top layer contains both fibroblast cells and cells sought to be grown. The lower layer of agarose, which is in contact with the upper layer, has suspended therein additional fibroblasts.

This two layer semi-solid agarose system provides an "environment" of feeder cells, i.e., the fibroblasts, which supports growth of the desired clones.

DETAILED DESCRIPTION

Complete culture medium was used and consisted of RPMI-1640 with the following supplements: 2mM L-glutamine, 1mM MEM sodium pyruvate, 1.01mM MEM nonessential amino acids, $5 \times 10^{-5}$M 2-mercaptoethanol, 100 μg/ml streptomycin, 100 units/ml penicillin, and 9% fetal bovine serum (unless other specified). MEM supplemented with 5% FBS was used for culture of fibroblasts.

Human mononuclear cells were separated from heparinized blood of donors immunized with irradiated melanoma cells on a Lymphoprep gradient. PBL from other appropriately immunized individuals have also been employed successfully. B lymphocytes were subsequently isolated by panning on Petri dishes coated with rabbit anti-human gamma globulin (10 ug/ml in phosphate buffer saline). Unattached cells were removed from the dishes, and 5 ml of supernatant from the EBV-infected cell line, B 95-8, were added to the B cells. The dishes were incubated overnight at 37° C. The cells were then harvested and plated at a concentration of $0.5-1\times10^4$ per well in 96-well tissue culture plates containing irradiated fibroblasts. Cells were fed twice a week with complete culture medium. When grown to $10^5$ cells/well, individual supernatants were tested by cytotoxicity assay for antibody production to HLA antigens. Subsequently, clusters of cells from positive wells were transferred into separate wells of 96-well plates, cultured for three to four more weeks, and cells from the wells still positive in cytotoxicity assay were used for cloning.

Before cloning, EBV-transformed cells were centrifuged on a lymphoprep gradient, washed twice in RPMI-1640, suspended in complete culture medium, and counted. To prepare the lower layer of agarose, six vol of fibroblasts suspended in complete culture medium with 15% FBS prewarmed to 40°-41° C. were added to 1 vol of prewarmed (40°-41° C.) 3.5% (wt/vol) agarose in double distilled water. The cells and agarose were mixed thoroughly, and samples of 0.5 ml, containing $5\times10^4$ fibroblasts were added to each well in twenty-four-well plastic tissue culture plates. The agarose was allowed to gel at 4° C. for 20 min. The upper layer of agarose was prepared in the following way: irradiated (1650 rads) fibroblasts and EBV-transformed cells were suspended in 9 vol of prewarmed (40°-41° C.) complete culture medium with 15% FBS and mixed thoroughly with 1 vol of 3.5% prewarmed agarose and samples of 1.0 ml containing a precise number of lymphoblastoid cells in a range of $10^2$ and $10_3$ cells, plus $5\times10^4$ fibroblasts, were poured on top of the bottom layer of agarose. This second layer of agarose plus cells was also allowed to gel, by refrigerating the plates for 15-20 min. The plates were subsequently transferred to a humidified tissue culture incubator with 5% $CO_2$ at 37° C., and the cultures were fed weekly with 0.1-0.15ml/well of 0.35% agarose (prepared by mixing 9 vol of complete culture medium with 15% FBS and 1 vol of 3.5% agarose). The newly added agarose was not allowed to gel. The number of clones were counted on the 21st day after initiation of cultures.

Human embryonic, pulmonary fibroblasts Flow No. 5000 or human foreskin fibroblasts Fogh-2 were cultured in MEM medium supplemented with 5% FBS in flasks. When confluent, cells were treated for 2-3 min with prewarmed (37° C.) solution of Trypsin-EDTA: 0.5 g trypsin (1:250) and 0.2 g EDTA/L. Subsequently, complete culture medium with 20% FBS was added. The cells were collected by centrifugation and passaged into new flasks for further culture. Alternately 2 to $4\times10^6$ cells per vial were frozen using 1.0 ml of complete culture medium with 25% FBS and 10% dimethylosulphoxide, and stored in liquid nitrogen. To be used as suspension cells in agarose, fibroblasts were thawed out immediately before use. Cells from 1-2 vials were centrifuged in cold RPMI-1640 for 10 min, suspended in 6 ml of complete culture medium with 9% FBS, vortexed to yield single cells, counted and split into two parts. Both samples were kept on ice for 1-2 hr. Subsequently, one sample was irradiated with 1650 rads with a gamma-emitting source and used as feeder cells in the upper layer of agarose. The second sample of non-irradiated fibroblasts was included in the lower layer of agarose.

Fibroblasts proliferate only when attached to a solid stratum, but do not grow in suspension. Thus, their use in agarose medium would not tend to overwhelm lymphoblastoid, or other cell types. This was proven by using $5\times10^4$ irradiated fibroblasts in the upper agarose layer, and $5\times10^4$ non-irradiated fibroblasts in the lower layer. No formation of fibroblast colonies was found.

Colonies were picked under a steroscopic microscope with Pasteur pipettes drawn out to fine tips. The agarose plugs were suspended individually in 0.2 ml of complete culture medium with 9% FBS, mixed in a Vortex, and plated on gamma-irradiated feeder layers of fibroblasts in 96 well flat-bottom culture plates. Cultures were fed twice a week with the same medium. Supernatants from individual wells were screened for the presence of antibody 3 to 4 weeks after plating.

Lymphoblastoid cells were the target cells in cytotoxicity tests. Cells were grown in complete culture medium with 9% FBS in flasks. They were purified by centrifugation on Lymphoprep gradient, washed twice in RPMI-1640, counted and suspended at a density $2\times10^6$ cells/ml in RPMI-1640 with 1% FBS. 2-3 $\mu$l of culture supernatant were added to each well of Terasaki plates followed by 1 $\mu$l of cells, and the mixture was incubated for 30 min at 4° C. Five $\mu$l of prescreened rabbit serum were added as a source of complement and plates were incubated for 45 min at 37° C. Subsequently, 8 $\mu$l of 0.2% trypan blue were added to visualize the cytotoxic effect, and the plates were read in the course of half an hour after the trypan blue addition. Wells with 40% or more stained cells were scored as positive.

The cloning frequency resulting from the thus described "double-layer method" was compared to a method known in the art, i.e., that described by Sugden and Mark, J. Virol. 23: 503-508 (1977), the "single layer method."

Two groups of lymphoblastoid cells were used in the comparison experiment: R-39.14, and Jebv. R-39.14 produces IgM (light chain K) cytotoxic antibody to human B cell surface ("HLA-D") antigen, and Jebv secretes immunoglobulin, although it is not known to produce specific antibody.

Table 1 sets forth the result of the comparison. Method "A" is single layer, while method "B" is double layer. Each of the cell lines has been maintained for more than a year.

TABLE 1

| | CLONING EFFICIENCY IN SINGLE LAYER (A) AND DOUBLE LAYER (B) METHOD USING "AGED" LYMPHOBLASTOID CELL LINES | | | |
|---|---|---|---|---|
| Cell line | Cloning method | Number of experiments | Percentage of clones (from-to) | Percentage of clones (mean) |
| R-39.14 | A | 4 | 0-0.05 | 0.012 |
| " | B | 8 | 2.7-24.6 | 11.22 |
| Jebv | A | 4 | 0-0.05 | 0.05 |
| " | B | 7 | 3.1-26.5 | 13.72 |

As will be seen, cloning efficiency (percentage of input cells giving rise to colonies of approximately 100 or more viable cells), increased from 0.012 to 11.22%, and from 0.05 to 13.72%.

A second set of experiments was performed, using recently transformed lymphoblastoid cells which had been in culture for less than two months. The lines R-59.81 and 422 are known to produce antibodies to an undefined human B cell antigen (R-59.81), and human cytomegalovirus (422). The same two methods were used, and the results are summarized in Table 2.

TABLE 2

CLONING EFFICIENCY IN SINGLE AND DOUBLE LAYER METHOD USING NEWLY ESTABLISHED LYMPHOBLASTOID CELL LINES

| Experiment No. | Cell line | Percentage of clones single layer | Percentage of clones double layer | Increase of efficiency |
|---|---|---|---|---|
| 1 | All-exp. 1 | 2.2 | 11.8 | 5.36 |
| 2 | R-59.81 | 4.6 | 13.1 | 2.84 |
| 3 | All-exp. 2 | 1.6 | 16.0 | 10.00 |
| 4 | 422-exp. 1 | 0.3 | 5.5 | 18.30 |
| 5 | SPL | 2.2 | 13.7 | 6.22 |
| 6 | 422-exp. 2 | n.t. | 9.5 | — |
| 7 | SD-02 | 0.3 | 7.0 | 23.3 |
| 8 | SD-04 | 1.0 | 9.8 | 9.8 |
| 9 | R-39.80 | 2.1 | 12.6 | 6.0 |
| 10 | SD-07 | 2.1 | 12.3 | 5.8 |
| 11 | MC-L | 2.8 | 11.25 | 4.0 |
| | Mean: | 1.92 | 11.14 | 9.1 |

Variations on the described methods are also possible. Experiments were done where fibroblasts were provided in the lower layer of agarose only, and the upper layer alone. These were used, together with the single layer method described supra, and the results are compared in Table 3. Additionally, these results were compared to results where fibroblasts were present in both layers.

TABLE 3

INFLUENCE OF UPPER AND LOWER LAYER ADDITION OF FIBROBLASTS ON CLONING EFFICIENCY

| Experiment No. | Cell Line | Percentage of Clones in Culture Type* | | | |
|---|---|---|---|---|---|
| | | A | B | C | D |
| 1 | R-39.14 | 0.0 | 4.3 | 5.0 | 10.8 |
| 2 | Jebv | 0.0 | 3.4 | 6.0 | 8.1 |
| 3 | SD-07 | 1.8 | 5.8 | 10.6 | 14.8 |
| 4 | SD-02 | 1.1 | 1.1 | 2.1 | 7.0 |
| 5 | R-39.80 | 2.1 | 1.6 | 5.0 | 12.6 |
| 6 | MC-L exp.1 | 2.8 | 4.5 | 7.5 | 11.25 |
| 7 | MC-L exp.2 | 2.0 | 4.6 | 5.6 | 10.62 |
| | Mean | 1.1 | 3.6 | 5.9 | 10.62 |

*Note:
A = Single layer method (Sugden and Mark)
B = Double layer method ($5.0 \times 10^4$ nonirradiated fibroblasts in lower layer only)
C = Double layer method ($5.0 \times 10^4$ irradiated fibroblasts in upper layer only)
D = Double layer method ($5.0 \times 10^4$ each of irradiated in the upper and nonirradiated fibroblasts in the lower layer)
t-Student test analysis; A:B $P \leq 0.013$; A:C $P \leq 0.001$ Large clone size is not reported in the table; however, it is worth noting. The double layer method facilitated picking of colonies 7-9 days earlier than in the previous method (i.e., after about 12-16 days of culture).

To determine if irradiated fibroblasts affect the method, experiments described in Table 4 were carried out. Cloning efficiency was only slightly higher when irradiated, rather than non-irradiated, fibroblasts were used. Hence, the choice of irradiated or non-irradiated fibroblasts does not affect the method.

TABLE 4

INFLUENCE OF IRRADIATED AND NONIRRADIATED FEEDER CELLS SEEDED IN UPPER LAYER OF AGAROSE ON CLONING EFFICIENCY IN DOUBLE LAYER METHOD

| Experiment No. | Cell Line | Percentages of Clones in Various Types of Cultures* | |
|---|---|---|---|
| | | A | B |
| 1 | MC-L | 11.25 | 10.1 |
| 2 | R-39.14 | 14.4 | 12.7 |
| 3 | SP-L | 13.7 | 11.4 |

*Setup of cultures:

| | A | B |
|---|---|---|
| Cells in upper layer: | Irradiated fibroblasts ($5 \times 10^4$ per well) | Nonirradiated fibroblasts ($5 \times 10^4$ per well) |
| Cells in lower layer: | Nonirradiated fibroblasts ($5 \times 10^4$ per well) | Irradiated fibroblasts ($5 \times 10^4$ per well) |

Table 5 demonstrates that the source of fibroblasts is not of great significance. Besides the fibroblast line used in earlier experiments, fibroblast line Fogh-2 was chosen at random, and these results show that this line performed with efficiency similar to that line used previously.

In order to determine the efficacy of the method in producing specific antibody producing cell lines, lymphocytes from melanoma patients undergoing immunotherapy with irradiated cultured melanoma cells were used as producers of antibodies to cell surface allo-antigens. Following EBV transformation, the cells were cultured for four weeks, and supernatants were screened by microcytotoxicity assays using the lymphoblastoid cells derived from the donors of the melanoma vaccine. Cells registering 40% or more cytotoxicity were cultured. These cells, designated R-59.81, which showed antibody positive in a screening, were cloned in agarose.

Table 6 shows that the double-layer method not only yields more viable colonies, but also improves dramatically the chances of deriving antibody-producing colonies. For example, the percentage of specific clones in single layer method=3.5%, while the percentage in double layer method=19% and 8.5%, respectively.

TABLE 5

INFLUENCE OF HUMAN FORESKIN FIBROBLASTS FOGH-2 ON CLONING EFFICIENCY IN DOUBLE LAYER METHOD

| Cell Line | Percentages of Clones |
|---|---|
| R-39.14 | 7.4 |
| Jebv | 20.5 |
| Mean: | 14.9 |

TABLE 6

CLONING IN DOUBLE LAYER METHOD AND ESTABLISHMENT OF SPECIFIC ANTIBODY PRODUCING LYMPHOBLASTOID CELL LINES

| Experiment No. | Cell line | Percentages of clones single layer method (sld) | Percentages of clones double layer method (dlm) | Yield of antibody producing clones (sld) | Yield of antibody producing clones (dlm) |
|---|---|---|---|---|---|
| 1 | R-59.81 | 4.2 | 13.1 | 1/28 (3.5%) | 12/63 (19%) |
| 2 | R-59.81 | n.t | 14.4 | — | 17/192 (8.5%) |

One skilled in the art will see the applicabilty of the method herein described to any type of cell, and particular, antibody producing cells, such as hybridomas, cells transformed by Epstein Barr Virus, such as human B cells and so forth. Specific examples of these would include cells producing antibodies to cytomegalovirus (CMV), or other viruses, cancer antigens, and so forth. These are, of course, merely examples and do not represent any limitation on the broad scope of the invention as described herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A method of increasing cloning frequency of human lymphocyte or lymphoblastoid cells which have been transformed with Epstein Barr virus comprising growing said transformed cells in a semi-solid agarose medium wherein a lower and an upper layer of agarose are used, said lower layer comprising fibroblasts suspended in the agarose layer and said upper layer comprising irradiated fibroblasts and the transformed cells suspended in the agarose layer wherein the upper agarose layer is added after the lower layer has gelled.

2. Method of claim 1, wherein said cells are human B cells.

3. Method of claim 1, wherein said cells are antibody producing cells.

4. Method of claim 1, wherein said cells are monoclonal antibody producing cells.

5. Method of claim 1, wherein said cells are lymphoblastoid cells which produce antibody to human B lymphocytes.

6. Method of claim 1, wherein said cells produce antibodies to virus antigens.

7. Method of claim 6, wherein said virus is cytomegalovirus.

8. A semi-solid agarose culture medium for growing cells comprising a lower and an upper layer of agarose, said lower layer comprising fiboblasts suspend in the agarose layer and said upper layer comprising irradiated fibroblasts and the cells suspended in the agarose layer wherein the upper agarose layer is added after the lower layer has gelled.

9. The culture medium of claim 8, wherein the cells are human lymphocyte or lymphoblastoid cells which have been transformed with Eptsein Barr virus.

* * * * *